(12) United States Patent
Reedy et al.

(10) Patent No.: US 10,858,309 B2
(45) Date of Patent: Dec. 8, 2020

(54) SYSTEM FOR PRODUCING REMOTE SENSING DATA FROM NEAR EARTH ORBIT

(71) Applicant: Skeyeon, Inc., San Diego, CA (US)

(72) Inventors: Ronald E. Reedy, San Diego, CA (US); Thomas E. Schwartzentruber, San Diego, CA (US)

(73) Assignee: Skeyeon, Inc., San Diego, CA (US)

(*) Notice: Subject to any disclaimer, the term of this patent is extended or adjusted under 35 U.S.C. 154(b) by 301 days.

(21) Appl. No.: 16/129,210

(22) Filed: Sep. 12, 2018

(65) Prior Publication Data

US 2019/0016672 A1 Jan. 17, 2019

Related U.S. Application Data

(63) Continuation of application No. 15/868,794, filed on Jan. 11, 2018, now Pat. No. 10,590,068, which is a
(Continued)

(51) Int. Cl.
*B64D 1/10* (2006.01)
*C07C 259/06* (2006.01)
(Continued)

(52) U.S. Cl.
CPC ............ *C07C 259/06* (2013.01); *A61P 35/00* (2018.01); *B64G 1/1021* (2013.01); *B64G 1/425* (2013.01);
(Continued)

(58) Field of Classification Search
CPC ............ H04B 7/18513; H04B 7/18515; H04B 7/18534; G01S 19/254; H04W 84/06;
(Continued)

(56) References Cited

U.S. PATENT DOCUMENTS

| 3,986,688 A | * | 10/1976 | Giragosian ............... B64C 3/48 244/219 |
| 4,754,601 A | | 7/1988 | Minovitch |

(Continued)

FOREIGN PATENT DOCUMENTS

| EP | 0668212 | 8/1995 |
| EP | 2853737 | 4/2015 |

(Continued)

OTHER PUBLICATIONS

Patent Cooperation Treaty, Notification of Transmittal of the International Search Report and the Written Opinion of the International Searching Authority, or the Declaration, Application No. PCT/US2019/013153, dated May 13, 2019, 17 pages.
(Continued)

*Primary Examiner* — Philip J Bonzell
(74) *Attorney, Agent, or Firm* — McAndrews, Held & Malloy, Ltd.

(57) ABSTRACT

A satellite system operates at altitudes between 180 km and 350 km relying on vehicles including an engine to counteract atmospheric drag to maintain near-constant orbit dynamics. The system operates at altitudes that are substantially lower than traditional satellites, reducing size, weight and cost of the vehicles and their constituent subsystems such as optical imagers, radars, and radio links. The system can include a large number of lower cost, mass, and altitude vehicles, enabling revisit times substantially shorter than previous satellite systems. The vehicles spend their orbit at low altitude, high atmospheric density conditions that have heretofore been virtually impossible to consider for stable orbits. Short revisit times at low altitudes enable near-real time imaging at high resolution and low cost. At such altitudes, the system has no impact on space junk issues of
(Continued)

traditional LEO orbits, and is self-cleaning in that space junk or disabled craft will de-orbit.

37 Claims, 8 Drawing Sheets

Related U.S. Application Data continuation-in-part of application No. 15/439,533, filed on Feb. 22, 2017, now Pat. No. 10,351,267.

(60) Provisional application No. 62/430,727, filed on Dec. 6, 2016.

(51) Int. Cl.

| | | |
|---|---|---|
| H04B 7/185 | (2006.01) | |
| G01S 19/39 | (2010.01) | |
| B64G 1/42 | (2006.01) | |
| B64G 1/10 | (2006.01) | |
| H04B 7/195 | (2006.01) | |
| B64G 1/44 | (2006.01) | |
| A61P 35/00 | (2006.01) | |
| G01S 13/90 | (2006.01) | |
| B64G 1/66 | (2006.01) | |

(52) U.S. Cl.
CPC .............. *B64G 1/443* (2013.01); *G01S 19/39* (2013.01); *H04B 7/18513* (2013.01); *H04B 7/195* (2013.01); *B64G 1/66* (2013.01); *B64G 2001/1028* (2013.01); *B64G 2001/1035* (2013.01); *G01S 13/90* (2013.01)

(58) Field of Classification Search
CPC .......... B64G 2001/1028; B64G 1/1021; B64G 1/1085; B64C 21/10; B64C 23/00
See application file for complete search history.

(56) References Cited

U.S. PATENT DOCUMENTS

| | | | |
|---|---|---|---|
| 5,433,726 A | 7/1995 | Horstein et al. | |
| 6,064,858 A | 5/2000 | Maatman et al. | |
| 6,145,298 A | 11/2000 | Burton, Jr. | |
| 6,834,492 B2 | 12/2004 | Hruby et al. | |
| 6,850,497 B1 | 2/2005 | Sigler | |
| 7,270,300 B2 | 9/2007 | Dressler | |
| 7,306,189 B2 | 12/2007 | Dressler | |
| 7,581,380 B2 | 9/2009 | Wahl | |
| 7,961,386 B2 * | 6/2011 | Danziger ............. B64G 1/1021 | |
| | | | 244/158.4 |
| 8,155,939 B2 * | 4/2012 | Hughes ................... G06F 30/20 | |
| | | | 703/6 |
| 8,312,704 B2 | 11/2012 | Keady | |
| 8,524,884 B2 * | 9/2013 | James ..................... C08B 37/00 | |
| | | | 536/55.1 |
| 8,723,422 B2 | 5/2014 | Diamant et al. | |
| 8,800,932 B2 | 8/2014 | Liu et al. | |
| 9,657,725 B2 | 5/2017 | Berl | |
| 9,723,386 B1 | 8/2017 | Ni et al. | |
| 9,796,487 B2 | 10/2017 | Yi et al. | |
| 2002/0041328 A1 | 4/2002 | Lecompte et al. | |
| 2003/0046921 A1 | 3/2003 | Hruby et al. | |
| 2004/0245407 A1 | 12/2004 | D'Ausilio et al. | |
| 2005/0060092 A1 | 3/2005 | Hablani | |
| 2005/0178919 A1 | 8/2005 | Dressler | |
| 2006/0030311 A1 | 2/2006 | Cruz et al. | |
| 2008/0237399 A1 | 10/2008 | Caplin | |
| 2008/0318022 A1 * | 12/2008 | James ................. C08B 37/0072 | |
| | | | 428/304.4 |
| 2009/0251773 A1 * | 10/2009 | Danziger ............. B64G 1/1021 | |
| | | | 359/367 |
| 2009/0312994 A1 * | 12/2009 | Hughes ................... G06F 30/20 | |
| | | | 703/6 |
| 2010/0045512 A1 | 2/2010 | Nelson | |
| 2010/0155524 A1 | 6/2010 | Maganas | |
| 2011/0192284 A1 | 8/2011 | Sawyer et al. | |
| 2012/0062100 A1 | 3/2012 | Liu et al. | |
| 2012/0193015 A1 | 8/2012 | Segal et al. | |
| 2012/0217348 A1 | 8/2012 | Martinez | |
| 2012/0307720 A1 | 12/2012 | Madsen et al. | |
| 2013/0102240 A1 | 4/2013 | Helfers | |
| 2015/0131703 A1 | 5/2015 | Balter | |
| 2015/0228471 A1 | 8/2015 | Shimoi et al. | |
| 2016/0094288 A1 | 3/2016 | Krebs | |
| 2016/0304220 A1 * | 10/2016 | Cecchini .................. B64G 1/44 | |
| 2017/0070939 A1 | 3/2017 | Chong et al. | |
| 2017/0192095 A1 | 7/2017 | Jobanputra et al. | |

FOREIGN PATENT DOCUMENTS

| | | |
|---|---|---|
| GB | 1181158 | 2/1970 |
| WO | 2017127844 | 7/2017 |

OTHER PUBLICATIONS

Patent Cooperation Treaty, Notification of Transmittal of the International Search Report and the Written Opinion of the International Searching Authority, or the Declaration, Application No. PCT/US2019/013149, dated Jan. 11, 2019, 21 pages.

Patent Cooperation Treaty, Notification of Transmittal of the International Search Report and the Written Opinion of the International Searching Authority, or the Declaration, Application No. PCT/US2017/064712, dated Jul. 23, 2018 (17 pages).

Aerospace America, published monthly by the American Institute of Aeronautics and Astronautics, Inc., Jan. 2015, vol. 53, No. 1, 68 pages.

Gravity Field and Steady-State Ocean Circulation Explorer; Wikipedia, the free encyclopedia; Retrieved from "http://en.wikipedia.org/w/index.php?title=Gravity_Field_and_Steady-State_Ocean_Circulation_Explorer&oldid=660976463"; Last updated May 5, 2015, 7 pages.

Natalia Mironova, African Farmers to Get NASA, NOAA Data on Their Phones (p. 6); Marc Selinger, A Stitch in Time for NASA Airplane Techies (p. 7); Marc Selinger, Satellite Pushed by Former VP Gore Ready for Launch (p. 8); Mark Williamson, Atmospheric Skimming Satellites (p. 9); Aerospace America; Jan. 2015, pp. 6-9; 4 pages.

Lake A. Singh; Very Low Earth Orbit Propellant Collection Feasibility Assessment; A Dissertation Presented to The Academic Faculty; Georgia Institute of Technology; Dec. 2014; 225 pages.

D. Di Cara, J. Gonzalez Del Amo, A. Santovicenzo, B. Carnicero Dominguez, M. Arcioni and A. Caldwell, I. Roma; RAM Electric Propulsion for Low Earth Orbit Operation: an ESA Study; IEPC-2007-162; Presented at the 30th International Electric Propulsion Conference, Florence, Italy; Sep. 17-20, 2007; 8 pages.

Tony Schonherr, Kimiya Komurasaki, Francesco Romano, Bartomeu Massuti-Ballester, and Georg Herdich; Analysis of Atmosphere-Breathing Electric Propulsion; IEEE Transactions on Plasma Science, vol. 43, No. 1, Jan. 2015, 8 pages.

D. Di Cara, J. Gonzalez del Amo, A. Santovincenzo, B. Carnicero Dominguez, M. Archioni, and A. Caldwell, and I. Roma; RAM Electric Propulsion for Low Earth Orbit Operation: an ESA study; IEPC-2007-162; Presented at the 30th International Electric Propulsion Conference, Florence, Italy; Sep. 17-20, 2007; 8 pages.

G. Cifali, T. Misuri, P. Rossetti, M. Andrenucci, D. Valentian, and D. Feili; Preliminary characterization test of HET and RIT with Nitrogen and Oxygen; 47th AIAA/ASME/SAE/ASEE Joint Propulsion Conference & Exhibit; Jul. 31-Aug. 3, 2011, San Diego, California; AIAA 2011-6073; 16 pages.

Kazutaka Nishiyama; Air Breathing Ion engine Concept; 54th International Astronautical Congress of the International Astronautical Federation, the International Academy of Astronautics, and the International Institute of Space Law; Sep. 29-Oct. 3, 2003, Bremen, Germany; IAC-03-S.4.02; 8 pages.

(56) References Cited

OTHER PUBLICATIONS

Kazutaka Nishiyama, Hitoshi Kuninaka, Yukio Shimizu, Kyoichiro Toki; 30mN-Class Microwave Discharge Ion Thruster, Institute of Space and Astronautical Science, IEPC 2003-62, 10 pages.

H.W. Loeb, G.A. Popov, V.A. Obukhov, D. Feili, Ch. Collingwood, and A. Mogulkin; Large Radio Frequency Ion Engines, Электронный журнал «Труды МАИ», Выпуск № 60—Russian translation: "Electronic Journal "Proceedings of the MAI" Issue No. 60" 8 pages.

Kevin D. Diamant; A 2-Stage Cylindrical Hall Thruster for Air Breathing Electric Propulsion; 46th AIAA/ASME/SAE/ASEE Joint Propulsion Conference & Exhibit; Jul. 25-28, 2010, Nashville, TN; AIAA 2010-6522; 9 pages.

Kevin D. Diamant; Microwave Cathode for Air Breathing Electric Propulsion; Presented at the 31st International Electric Propulsion Conference, University of Michigan, Ann Arbor, Michigan, USA; Sep. 20-24, 2009; IEPC-2009-015; 11 pages.

Kazuhisa Fujita; Air Intake Performance of Air Breathing Ion Engines; vol. 52, No. 610, pp. 514-521, 2004; 8 pages.

Leonid Pekker and Michael Keidar; Analysis of Airbreathing Hall-Effect Thrusters; Journal of Propulsion and Power; vol. 28, No. 6, Nov.-Dec. 2012; 7 pages.

Thomas John McGuire; Aero-Assisted Orbital Transfer Vehicles Utilizing Atmosphere Ingestion; Thesis submitted to the Department of Aeronautics and Astronautics; Jun. 8, 2001, 133 pages.

L. Garrigues; Computational Study of Hall-Effect Thruster with Ambient Atmospheric Gas as Propellant; Journal of Propulsion and Power; vol. 28, No. 2, Mar.-Apr. 2012; 11 pages.

Angelo Cervone, Barry Zandbergen, Jian Guo, Eberhard Gill, Wolter Wieling, Flavia Tata Nardini, and Coen Schuurbiers; Application of an Advanced Micro-Propulsion System to the Delffi Formation-flying Demonstration Within the QB50 Mission; 63rd International Astronautical Congress, Naples, Italy. Copyright © 2012 by the International Astronautical Federation; IAC-12-C4.6.2; 8 pages.

* cited by examiner

SYSTEM FOR PRODUCING REMOTE SENSING DATA FROM NEAR EARTH ORBIT

CROSS-REFERENCE TO RELATED APPLICATIONS

This application is a continuation application of U.S. patent application Ser. No. 15/868,794, filed Jan. 11, 2018, entitled "System For Producing Remote Sensing Data From Near Earth Orbit," which claims priority to U.S. Provisional Patent Application Ser. No. 62/430,727, filed Dec. 6, 2016, entitled "A Satellite System" and U.S. patent application Ser. No. 15/439,533 filed on Feb. 22, 2017, entitled "A Satellite System". The entirety of U.S. Provisional Patent Application Ser. No. 62/430,727, U.S. patent application Ser. No. 15/439,533 and U.S. patent application Ser. No. 15/868,794 are incorporated herein by reference.

BACKGROUND

Satellites are used in many aspects of modern life, including earth observation and reconnaissance, telecommunications, navigation (e.g., global positioning systems, or "GPS"), environmental measurements and monitoring and many other functions. A key advantage of satellites is that they remain in orbit due to their high velocity that creates an outward centripetal force equal to gravity's inward force. Therefore, once in orbit, they stay there typically for years or decades. Since the velocities are so high (e.g., 3-8 km/s, depending on altitude), atmospheric drag should be minimized and/or avoided, which means satellites typically operate outside virtually any trace of the particles that constitute the atmosphere. In addition to drag, atmospheric collisions with particles, even at trace concentrations, can overheat, damage or eventually destroy the satellite.

Satellites are therefore clearly differentiated from atmospheric flying (i.e., airborne) vehicles such as airplanes, unmanned aerial vehicles (UAVs), helicopters or balloons, in which the atmosphere supports lift and the vehicles operate at velocities typically between zero (i.e., hovering) to 1-3 times the speed of sound and at altitudes below about 35 km.

Satellite orbital heights are typically categorized in three broad segments: low earth orbit (LEO), medium earth orbit (MEO) and geostationary earth orbit (GEO). The general uses and characteristics of these orbits are shown in Table I and represent generally accepted usage of the terms LEO, MEO and GEO. Satellites can orbit at any altitude above the atmosphere, and the gaps in altitude shown in Table 1, such as between LEO and MEO, are also used, if less regularly. It is also common that satellites may orbit in eccentric, non-circular orbits, thereby passing through a range of altitudes in a given orbit.

TABLE I

Typical characteristics of common orbits.

| Orbit | Altitude, km | Velocity, km/s | Exemplary Uses | Comments |
|---|---|---|---|---|
| LEO | 400-2,000 | 6.9-7.8 | Earth observation, sensing, ISS, telecom constellations | Random orbits, 3-10 Y lifetime, space junk issue, little radiation |
| MEO | 15,000-20,000 | 3.5 | GPS, GLONASS, Earth observation | Highest radiation (Van Allen Belt), equatorial to polar orbits |
| GEO | 42,000 | 3.1 | Sat TV, high BW telecom, weather satellites | Can remain above same spot on Earth, typically equatorial orbits |

For most satellites, their useful lifetime is determined by multiple factors. For example, in the case of GEO satellites, small fluctuations in solar winds and earth's gravity require regular use of fuel to maintain the satellite's position and attitude. Once exhausted of fuel, a satellite is typically rendered useless and decommissioned. However, due to GEO height, such a satellite itself will stay in orbit virtually forever due to its altitude and near zero atmospheric drag. Due to their apparent stationary position as viewed from earth's surface, they are widely used for telecommunications and satellite TV. Their large distance from Earth limits their usefulness in telephone services (time delay) and in high-resolution imaging (distance). They encounter solar winds and cosmic radiation that force use of very specialized and expensive electronics to survive.

MEO satellites are in the mid-range, mostly similar to GEO satellites except that they do not appear stationary when viewed from earth's surface. Their most common usage is for satellite positioning services, such as GPS, and certain Earth observation missions for which their trade-off in altitude between GEO and LEO is beneficial. Due to the presence of the so-called Van Allen Belts, these satellites can suffer large amounts of radiation and therefore require very specialized and expensive electronics to survive.

LEO satellites, conversely, may be in a constant state of very slight atmospheric drag requiring either regular boost to their altitude (e.g. fuel burns of typically chemical engines) or an end-of-useful-life caused by reentry and burn up similar to a meteor entering the earth's atmosphere. As an example, the International Space Station (ISS), orbiting at about 425 km, loses approximately 2-4 km/month of altitude and requires regular fuel burns to ensure it stays in proper orbit. But the atmospheric drag is still very low and LEO satellites can remain in orbit for years without fuel burns.

This relatively long life is the source of so-called "space junk", in which any orbiting device can potentially collide with a useful satellite, thereby damaging or destroying it and creating additional orbiting objects. It is a widely recognized issue that at some density of space junk, probabilities of collisions increase, eventually leading to a virtually unusable orbit. A beneficial element of the current invention is to provide satellite services without increasing the space junk issue and furthermore to enable a mechanism that will be "self-cleaning" in the chosen orbits of 180-350 km.

Due to various shielding effects, especially of earth's magnetic fields, LEO satellites encounter little radiation and therefore do not necessarily require specialized and expensive electronics to survive. An exception to this rule is the so-called South Atlantic Anomaly, or SAA, which is a region in which a higher density of energetic particles may be found, causing short term interruptions of some electronics. This effect can be mitigated by many known techniques, so does not present a large issue for LEO satellites.

In fact, continual improvement in system operation is realized since by lowering the operating altitude, system components (e.g. optics, electronics, synthetic aperture radar (SAR), required solar panel area, etc.) can be made smaller, which in turn reduces vehicle size and drag, thereby enabling an even lower operating altitude, and so-on. While it is desirable to be closer to earth's surface (or any celestial body's surface, say Mars), atmospheric density effectively sets a lower limit on orbital altitude; or forces expensive, heavy counteracting systems such as on the Gravity field and steady-state Ocean Circulation Explorer satellite (GOCE), discussed below. For bodies without an atmosphere, such as earth's moon, there is no lower limit other than hitting the body itself.

SUMMARY

The present disclosure relates, generally, to satellite systems in a near earth orbit, and more particularly to a satellite system capable of high frequency, low latency data acquisition and transfer rates, the system occupying a near earth orbit.

As described below, a properly designed near earth orbit (NEO) vehicle must generate thrust to overcome the vehicle's drag on a regular basis. As used herein, Near Earth Orbiters (NEOs) describe the system and its constituent vehicles (i.e., a "NEO satellite system", "NEO vehicle" or a "NEO satellite") that operate in stable orbits at 180-350 km (e.g., below a typical LEO). Therefore, it is a purpose of this invention to describe a satellite system based on orbital vehicles operating in stable Earth orbits at altitudes well below traditional satellites, specifically between approximately 180 and 350 km.

The satellite system described herein employs a plurality of spacecraft configured to communicate with each other, as well as with terrestrial based receivers (e.g., ground and/or sea based antenna). In some examples, each spacecraft balances a variety of systems for sustained operation in a near earth orbit. For instance, drag is directly proportional to atmospheric density. Therefore, each spacecraft has a relatively small cross-sectional area facing the direction of travel compared to the total surface area, to reduce drag from collisions with atmospheric particles (e.g., oxygen, nitrogen, etc.). Each spacecraft has a volume sufficient to support data collection equipment (e.g., imaging and/or radar apertures), and a total surface area that is large relative to the direction of travel surface area support solar energy collection. Each spacecraft contains a means of propulsion, which can include an engine and/or a volume of engine propellant (e.g., compressed xenon housed in tanks).

Further, each spacecraft includes one or more surfaces with solar energy collection panels, to provide power to a rechargeable battery and/or to power one or more components of the spacecraft directly. In some examples, the solar panels are arranged about the spacecraft such that sunlight is collected from various angles while maintaining a static position of each solar panel relative to the spacecraft bus. In this manner, the solar panels act as passive aerodynamic control (i.e., "stability fins," in a swept-configuration, described in detail, below, with respect to one or more of the figures).

To achieve the multiple goals with a single vehicle, an example spacecraft is defined by a thin, long bus, with stability fins extending from the bus such that solar panels incorporated thereon are exposed to solar energy regardless of the angle of the spacecraft. In some examples, a sharp leading edge with a specialized coating may also be incorporated onto the spacecraft to reduce atmospheric drag. Further, the bus is capable of housing multiple components, including, but not limited to, transceivers, processors, imaging systems, positioning systems, and propulsion systems. In some examples, each spacecraft is capable of maintaining an orbit of about 220 km to 280 km from Earth or greater, for approximately three (3) years.

Figure 1:
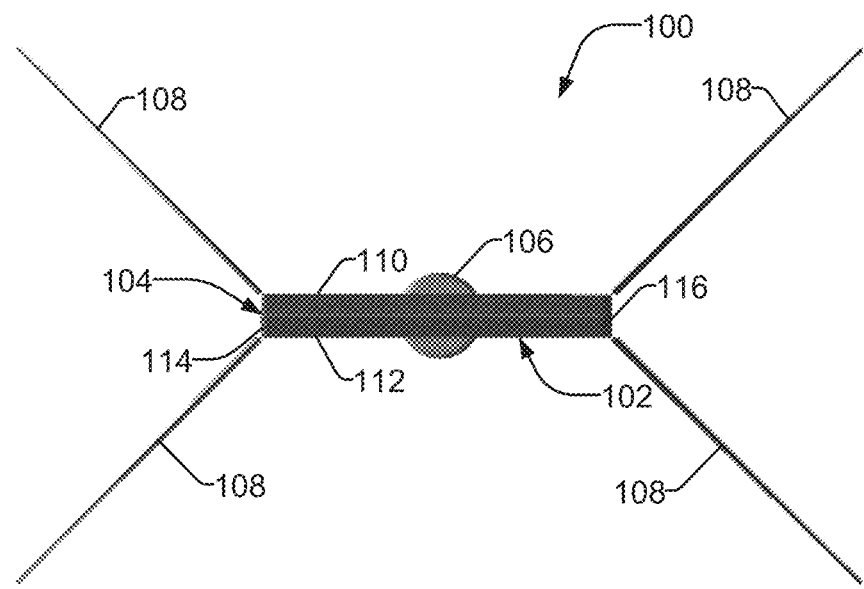
FIG. 1 shows an example satellite in accordance with aspects of this disclosure.

The several figures provided here describe examples in accordance with aspects of this disclosure. The figures are representative of examples, and are not exhaustive of the possible embodiments or full extent of the capabilities of the concepts described herein. Where practicable and to enhance clarity, reference numerals are used in the several figures to represent the same features.

DETAILED DESCRIPTION

This detailed embodiment is exemplary and not intended to restrict the invention to the details of the description. A person of ordinary skill will recognize that exemplary numerical values, shapes, altitudes, applications of any parameter or feature are used for the sole purpose of describing the invention and are not intended to be, nor should they be interpreted to be, limiting or restrictive.

The current disclosure relates to vehicles operating at altitudes between about 180 km to 350 km, what is defined herein as a Near Earth Orbiter (NEO), using thrusters for orbiting where atmospheric density is too high for traditional satellites and too low for airborne vehicles. To remain in stable orbit, the NEO satellite employs a propulsion system (e.g., electric or chemical propulsion engine) to generate thrust sufficient to overcome the vehicle's drag. An exemplary NEO satellite based on electric propulsion is described herein, but a person of ordinary skill in the relevant art will appreciate that other forms of propulsion are possible, such as chemical, optical or others that may be substituted and align with the scope of the present invention. The NEO satellite may be powered by solar energy and equipped with various data collection systems, data transmission and reception systems, data storage, power storage, as well as other systems.

The NEO satellite may include an attitude and orbit control subsystem consisting of sensors to measure vehicle orientation, control laws embedded in the flight software, and one or more actuators (e.g., reaction wheels, thrusters, etc.). These actuators apply the torques and forces needed to re-orient the vehicle to a desired attitude, keep the satellite in the correct orbital position, and keep antennas and sensors pointed in the right directions.

Additionally or alternatively, a thermal control subsystem can make adjustments to protect electronic equipment from extreme temperatures due to intense sunlight or the lack of sun exposure on different sides of the satellite's body (e.g. optical solar reflector). Another system is the communication payload, which is made up of transponders. A transponder is capable of receiving uplinked radio signals from earth satellite transmission stations (e.g., antennas; see FIG. 12), amplifying received radio signals, sorting the input signals, and directing the output signals through input/output signal multiplexers to the proper downlink antennas for retransmission to earth satellite receiving stations (e.g., antennas).

Some example satellites disclosed with respect to the current invention may orbit at altitudes below LEO (i.e., lower than 350 km). Due to atmospheric drag at these altitudes, thrust may be provided on a continuous or regular periodic basis or the vehicle's orbit will decay in a matter of days, weeks or months, depending on altitude. The NEO vehicle 100 described herein could be configured to provide sufficient thrust to maintain orbits between 180-350 km.

At altitudes lower than LEO, atmospheric density increases exponentially. Below an altitude of about 120 km, atmospheric density that causes atmospheric drag increases by an order of magnitude about every 20 km. Meanwhile, above that breakpoint and up to about 400 km, the atmosphere changes by an order of magnitude about every 50-75 km. The key effect is that atmospheric density, and therefore drag, is about five orders of magnitude higher at an altitude of 100 km compared to the altitude of the ISS at about 425 km. Furthermore, the high velocity collisions with residual atmospheric oxygen are highly destructive to vehicle components at this range. Accordingly, very few satellites operate below about 400 km, and those that do are often in highly elliptical orbits, thus spending very little time at the lower altitudes. Conventional satellite design assumes that the vehicle design itself has little or no effect on drag, which is a fair assumption for satellites operating at ISS altitudes and higher. Because of the rapid increase in drag below these altitudes, it has conventionally been thought that orbits in the zone of rapidly increasing drag had little utility, and systems have conventionally been designed to avoid these lower altitudes. Certainly, traditional satellite design is poorly suited to a high drag environment.

However, maintaining a lower altitude orbit is desirable for multiple reasons. For instance, any earth imaging application can get higher resolution images from a smaller, less complex imaging device simply by being closer to the surface. For example, if an optical imager is 3 times closer to its object, it will get approximately 9 times better resolution (i.e., in pixels per area) for a given optical system. Similarly, for telecommunications, due to the inverse square law relationship between radio frequency (RF) energy and distance, a transmitter that is 3 times closer will create 9 times stronger signal at a receiver, or require 9 times less power to achieve the same signal power at the receiver. Additionally, for an active radar application, being 3 times closer requires 81 times less power for equivalent performance due to the $1/r^4$ power law of radar (or 27 times less power for SAR, due to the associated $1/r^3$ power law). All of these factors enable the exemplary NEO vehicle to reduce the size and cost of a NEO satellite system sufficiently to enable large satellite constellations that have short revisit times at affordable cost.

FIG. 1 illustrates, in a front view, an exemplary version of a NEO vehicle 100. The NEO vehicle 100 can further include an electric propulsion engine 106 to generate thrust by, for example, ionizing and accelerating a propellant gas to counteract drag, in order to maintain the desired orbit. Additionally or alternatively, the engine 106 can be comprise an engine with chemical thruster capabilities, such as a micro-thruster type engine. Although represented as being external to the vehicle bus 102, the engine 106 can be integrated within the bus 102, shielded by one or more panels of the bus 100, and/or dimensioned to extend beyond a surface of the bus 102, in accordance with the present disclosure. One or more stabilization surfaces or panels 108 can be employed, designed to enhance the stability of the NEO vehicle 100, as well as support solar paneling to collect power. The NEO vehicle 100 is defined by a narrow cross section, as exemplified in vehicle bus 102. The bus 102 includes a first or top panel 110, a second or bottom panel 112, and lateral sides 114 and 116. At the nose of the NEO vehicle 100 is a leading edge 104, which is configured with a bevel to slope toward one or both the first or second panel 110, 112.

Figure 2:
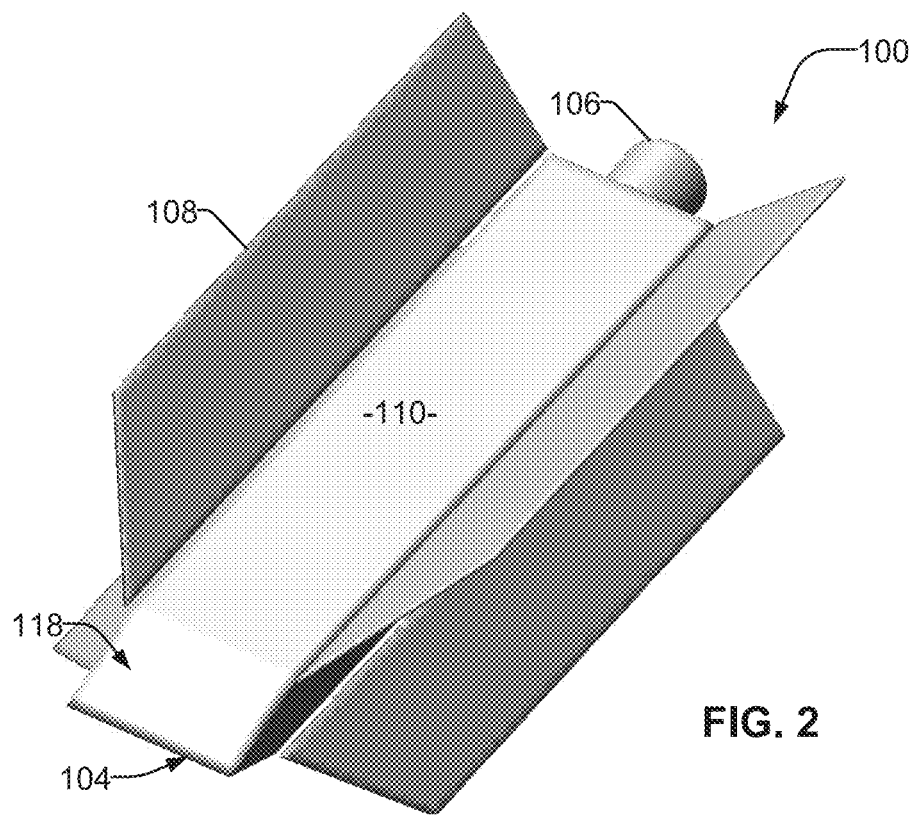
FIG. 2 shows a perspective view of an example satellite in accordance with aspects of this disclosure.

The example NEO vehicle 100 of FIG. 2 is shown in perspective view, illustrating a bevel 118 sloping from the leading edge 104 to the panel 110. In some examples, the bevel 118 is angled at 20 degrees, and another bevel opposite bevel 118 slopes toward panel 112. In some examples, the angle is greater than or less than 20 degrees. In examples, the bevel 118 slopes at a first angle, whereas the opposite bevel slopes at a second angle different from the first angle. Furthermore, the bevel can slope at a constant angle on a flat surface, or can progress at a varying gradient toward the panels 110, 112. Other variations on the surface of the bevel can also be employed, including ovoid-conical shape, pyramidal shape, etc., with the key feature being that the frontal area is sharply angle along the direction of travel. As described herein, the small cross section of the NEO vehicle 100, as well as the sloping bevel from the leading edge 104, reduces drag on the vehicle 100 from atmospheric particles and aids in maintaining stable orientation in orbit.

Figure 3A:
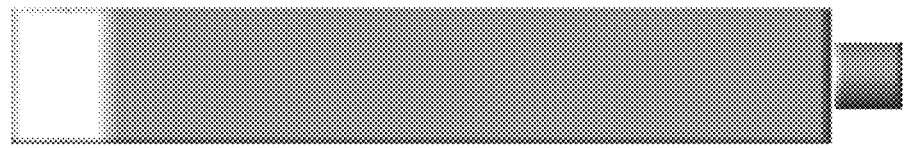
FIGS. 3A-3C show example satellite configurations in accordance with aspects of this disclosure.
Figure 3C:
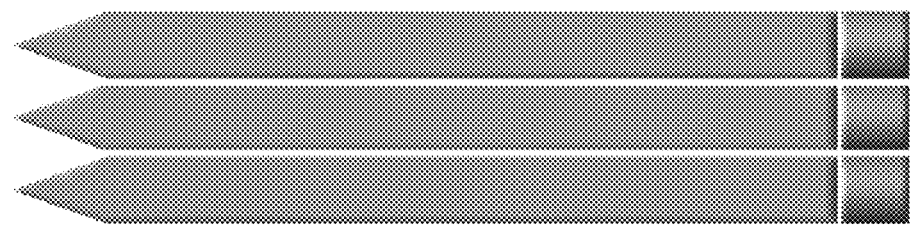
Figure 3B:
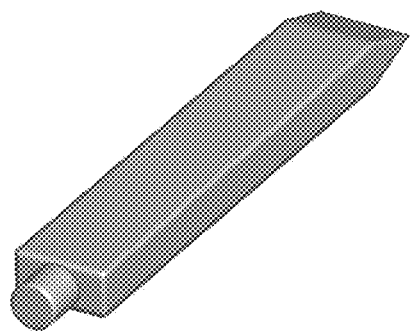
Figure 4:
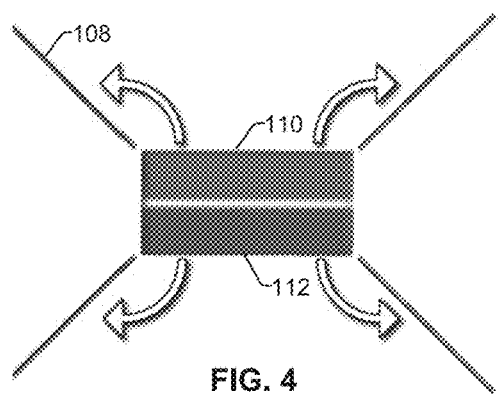
FIG. 4 shows an example satellite deploying a solar collection system in accordance with aspects of this disclosure.

FIGS. 1 and 2 illustrate a NEO vehicle 100 in a deployed configuration. FIGS. 3A-3C show example satellite configurations for storage and/or transport, in accordance with aspects of this disclosure. For instance, FIG. 3A is a view from the top or bottom of the NEO vehicle 100, whereas FIG. 3B shows a perspective view from the rear of NEO vehicle 100. FIG. 3C shows a stack of three NEO vehicles, which can be arranged in a tight grouping for efficient transport on a launch satellite. Once the launch satellite delivers the vehicle(s) to an appropriate orbit, the configuration changes to operational. In the example of FIG. 4, the NEO vehicle 100 deploys the support panels 108 (housing the solar collection system). As shown, the panels 108 are secured or otherwise arranged tightly against the NEO vehicle body 102 during storage/transport, such that a pair of panels 108 are unfolded from each of the first surface 110 and the second surface 112. In some examples, a light baffle is further deployed once the vehicle is delivered in the proper orbit (see, e.g., FIG. 9).

Figure 5:
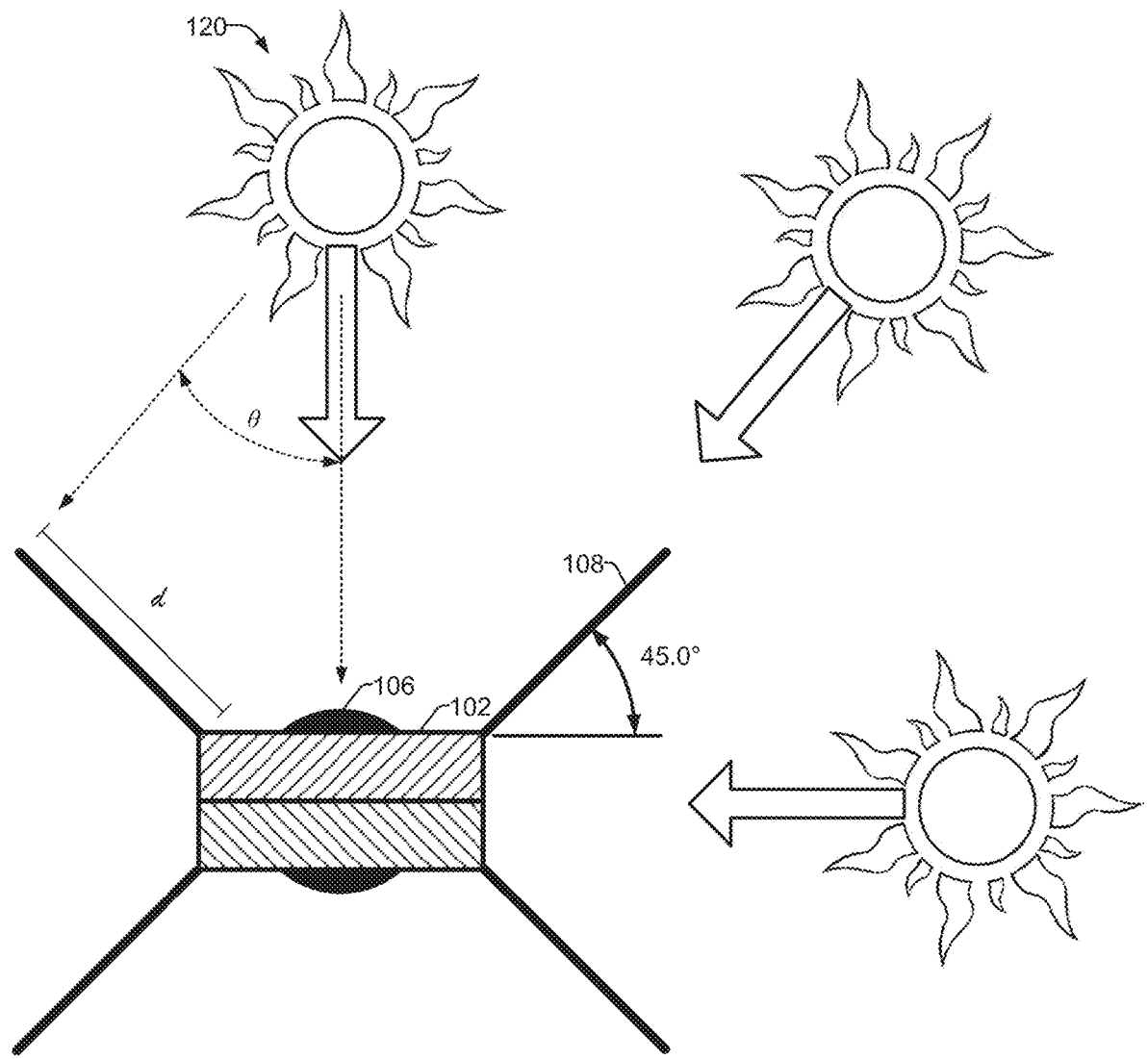
FIG. 5 shows another example satellite in accordance with aspects of this disclosure.

Stabilization surfaces/panels 108 can be arranged to extend from the vehicle bus 102 to both minimize drag on the vehicle and to maximize energy capture by solar paneling mounted thereon. In the example of FIG. 5, the NEO vehicle 100 includes four panels 108 arranged at an angle from the horizontal plane. This arrangement provides for maintained exposure of at least two solar collection surfaces regardless of vehicle 100 orientation relative to the sun 120. Thus, at a 45 degree angle, a panel 108 would have an effective radiation exposure in accordance with the following equation:

$$d \times \cos\theta$$

where d is the length of the panel and $\theta$ the angle of incidence of the solar rays relative to the panel normal direction. Although shown in a particular arrangement, the panels 108 can be angled in any manner with respect to the vehicle bus 102. Further, the panels 108 can be deployed in a fixed position, or can be movable to maximize exposure to the sun 120. In some examples, movement of the panels 108 can be commanded by a controller, such as to turn a motor, or in response to a sensor configured to track the intensity of the sun's rays. In some examples, the satellite bus panels 110, 112, 114, 116 can also support solar cells. Of note in this design is that in all cases, the large panels are presented edge on to the direction of travel, which substantially reduces drag effects from the panels relative to presenting the solar surface to the direction of travel, and indeed the small frontal cross section of the vehicle shown in FIG. 1 relative to its overall dimensions and volume is an important aspect of the inventive design.

Figure 6:
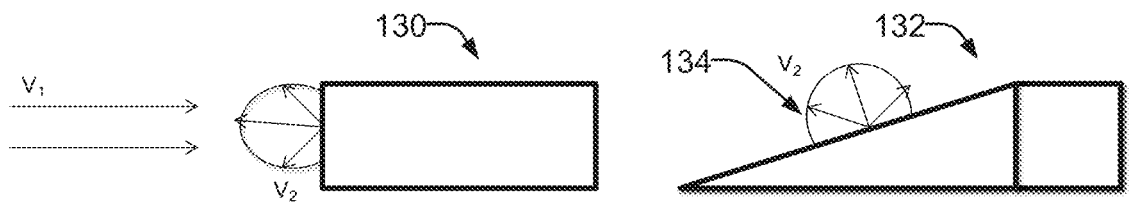
FIG. 6 shows a cross-section of an example forward surface of a satellite in accordance with aspects of this disclosure.

FIG. 6 shows a side-view of an example forward surface of a satellite with a drag analysis represented as a vector. For instance, the leading edge of object 130 experiences significant drag force, shown as particles rebound at a vector $V_2$ in response to particles travelling toward the object 130 at a velocity $V_1$. Object 132 experiences a less direct effect 134, as the direction of the reflected particles (shown as vectors 134, $V_2$) are directed at generally more diffuse angles than object 130.

Unlike traditional atmospheric drag cases for controlled flight in the atmosphere, drag at these altitudes is a function of particle density, speed, and the mechanism by which those particles interact with the satellite vehicle. Some particles will "bounce" off the drag surface in "reflective" collisions, which do not result in the full transfer of momentum from the vehicle to the particle, and the particle retains a large vector $V_2$ relative to its original pre-collision vector $V_1$. Other collisions are "thermally accommodative", meaning that the particle is effectively trapped or absorbed by the surface, with a full transfer of momentum and energy that results in the particle leaving the surface with a small residual vector $V_2$ relative to the drag surface. The latter collisions have a higher contribution to drag. Conventional orbital vehicle design does not account for or design against the two types of drag inducing collisions.

Figure 7:
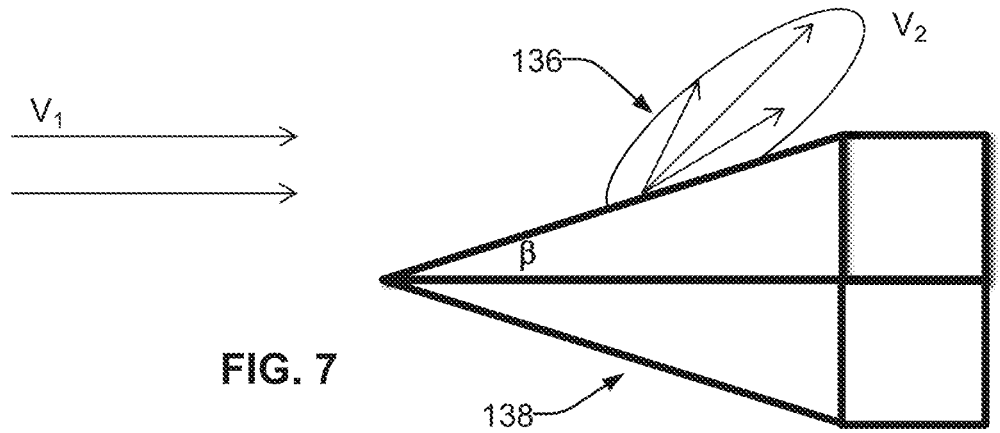
FIG. 7 shows a cross-section of another example forward surface of a satellite in accordance with aspects of this disclosure.

The objects 130, 132 shown in FIG. 6 are representations of a typical satellite surface material that exhibits diffuse reflection and full thermal accommodation drag proportional to $(V_1-V_2)$, which is approximately equal to $V_1$, as $V_1$ is much greater than $V_2$. FIG. 7, by contrast, exhibits the interaction of a front edge/bevel of a NEO vehicle 100 with a surface treatment and/or selected material, as descried herein. An example of such materials and possible applications are described in co-pending application No. 62/616,325, entitled "Atomic Oxygen-Resistant, Low Drag Coatings And Materials," to Timothy Minton and Thomas E. Schwartzentruber. For instance, the object 138 is coated with an advanced material (e.g., such as SiOx), which results in a partial specular reflection (shown by vector $V_2$, 136) and low thermal accommodation. The presentation of angled surfaces in the direction of travel, on the one hand, plus the use of materials that exhibit reflective properties with respect to residual atmospheric particles, on the other, result in drag on the object 138 (e.g., the leading edge and bevel of NEO vehicle 100) that is much lower, as $V_1$ can be comparable to $V_2$ in magnitude.

In one example, different surface treatments or materials are used for the exterior of the satellite system. For example, atomically smooth materials such as sapphire or other polished materials may be used, where interactions with atmospheric particles would be similar to specular reflection. Accordingly, the endurance of the NEO vehicle 100 may exceed that of traditional satellites. In the case of a NEO vehicle 100 operating with an ion engine, interaction with oxygen, and to some degree nitrogen, may limit endurance of the system. Such issues may be mitigated significantly, for example, by proper choice of materials. For example, metallic elements, such as heavy, noble metals like gold do not oxidize and are less susceptible to sputtering than other materials. New synthetic materials or high strength ceramics may also be used.

In some examples, advanced materials are used to reduce drag from atmospheric particles. For instance, the use of advanced materials combined with a beveled (i.e. sharp) leading edge can reduce the drag experienced by the satellite system by approximately a factor of two. Importantly, the mass and volume needed to maintain orbit of the satellite system decreases, as much as half. Similarly, the mission lifetime for the system could be doubled. The improvement can also have an impact on safety factors for endurance and weight.

Figure 8:
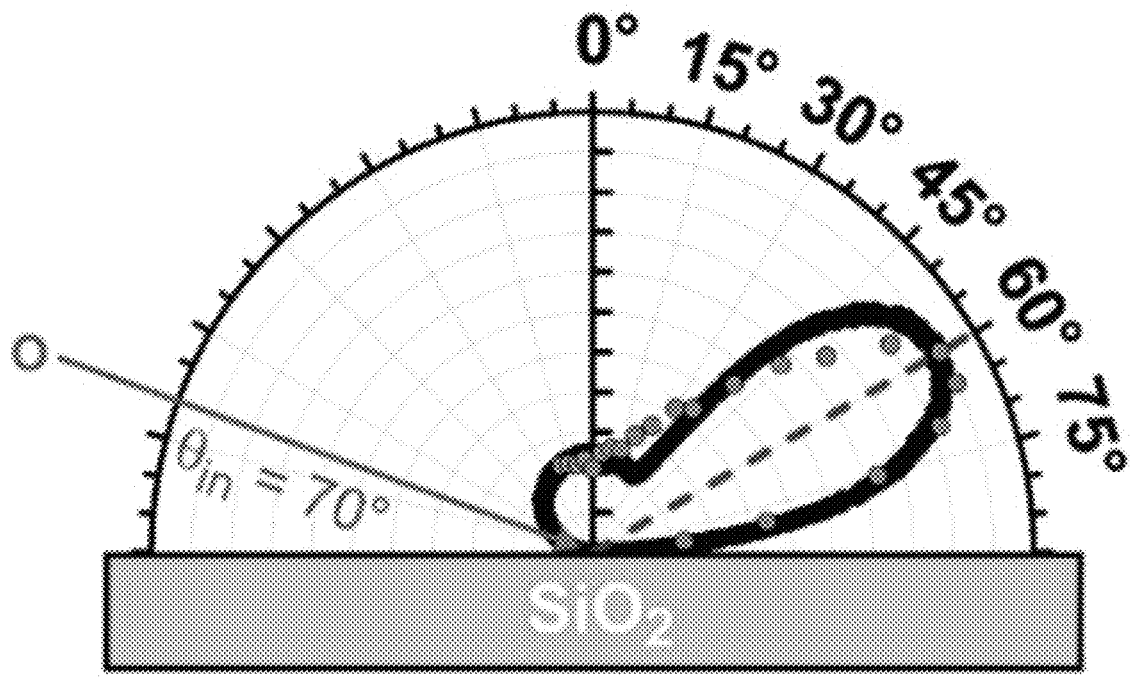
FIG. 8 illustrates graphical data of air particle interaction within an example satellite in accordance with aspects of this disclosure.

FIG. 8 illustrates graphical data of air particle interaction in accordance with aspects of this disclosure. At altitudes of 180-350 km, earth's atmosphere is made up primarily of O, $O_2$, N and $N_2$. In an example where the NEO vehicle 100 orbits the Earth at about 200 km, the NEO vehicle 100 has an orbital velocity of about 7.8 km/sec, these atom and molecule species have a velocity relative to the vehicle of the same 7.8 km/sec. The drag analysis presented in FIG. 8 shows a molecular beam of oxygen atoms (O), traveling at approximately 8 km/s. The molecular beam impacts the SiO2 surface at approximately a 20-degree angle. The narrow scattering distribution is centered at approximately 30 degrees. Accommodation is low, with an $E_{out}/E_{in}$=60-

80%. Thus, the application of a SiOx coating and angled incidence has a meaningful reduction in drag versus traditional materials, on the order of one-half the drag experienced by a diffuse material without a beveled (i.e. sharp) leading edge.

Figure 9:
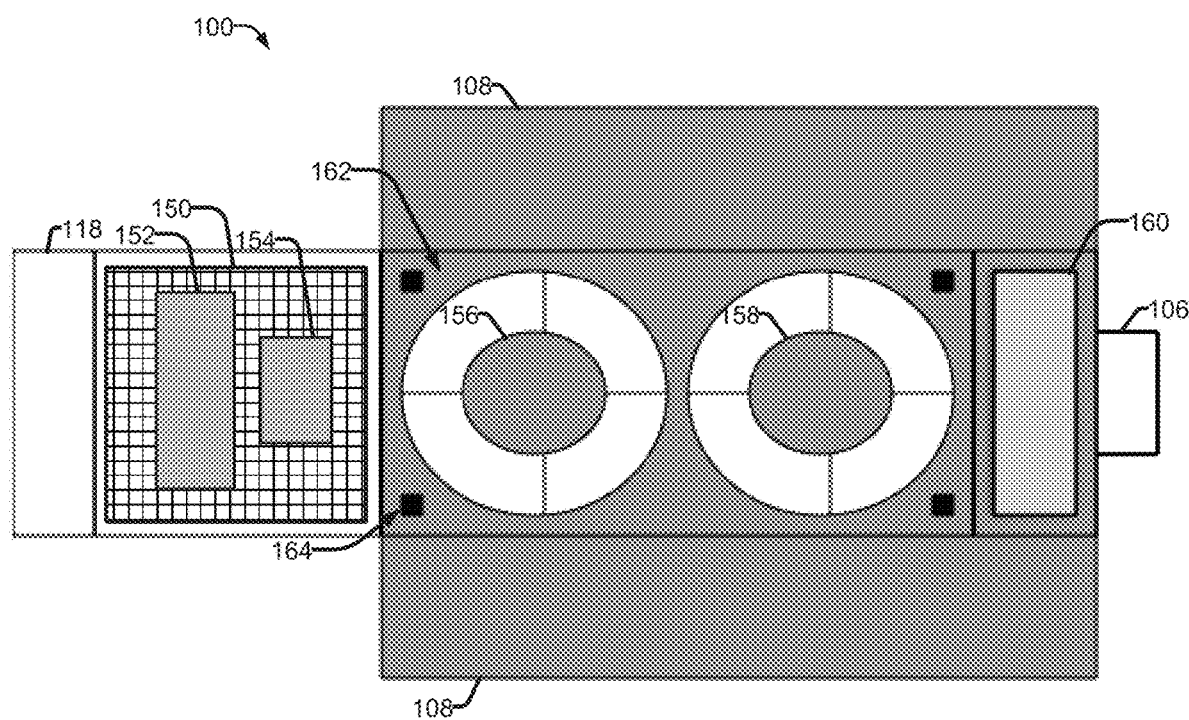
FIG. 9 shows a cross-section of an example satellite illustrating various components in accordance with aspects of this disclosure.

FIG. 9 shows a view of an example NEO vehicle 100 with the bottom surface removed to expose various components therein. As shown in FIG. 9, a radio frequency antenna 150 (e.g., a phased array) can be included. An example of such a system and possible applications are described in co-pending application Ser. No. 15/868,812, entitled "Radio Frequency Data Downlink For A High Revisit Rate, Low Earth Orbit Satellite System," to Daniel Nobbe and Ronald E. Reedy. A computing platform 152 can include a processor, memory storage, and/or various sensor types. Attitude control gyroscopes and/or reaction wheels can be included. A battery 154 or other storage system (e.g., capacitor, etc.) can be used to store power collected by solar panels in order to, for example, power the various components and the electronic engine 106 of the NEO vehicle 100.

One or more optical imaging systems/lenses 156,158 are also included (e.g., variable field of view, multispectral imaging, etc.). The lenses 156, 158 are configured to have a thickness sufficient to provide detailed imaging (e.g., a 1 m resolution at NEO altitudes) yet thin enough to fit within the vehicle bus 102, along with the various other components. A folded light path contributes to reduced thickness of an optical assembly, while a radar assembly can be made from an array similar to the radio phased array antenna. Additionally or alternatively, the imaging system can include a mechanical device to control the orientation of the lenses 156, 158 to adjust the focus of the imaging system. A baffle 162 can be used to provide stability as well as filtering stray light effects from non-imaged sources, supported by one or more posts 164. Each spacecraft is configured with sufficient area/volume to house one or more imaging systems, such as two camera lenses 156, 158, and one or more baffles 162. In some examples, a camera lens can be a 10 cm thick optical lens system, and a baffle external to the vehicle bus is used.

Many aspects of the spacecraft have equal applicability for systems configured for image capture (e.g., optical data collection) and radar capable spacecraft. In some examples, considerations related to size of the vehicle, weight, drag, power demands, as well as propellant needs, may change based on these and other factors. For example, in some embodiments, the cross-sectional area for an imaging satellite is greater than that for a radar capable satellite (e.g., about 5 cm thick vehicle bus for radar satellite, compared with about 10 cm thick to house the camera optics).

Additional and alternative components may be included in the NEO vehicle 100, such as radar or radio components, sensors, electronics bays for electronics and control circuitry, cooling, navigation, attitude control, and other componentry, depending on the conditions of the orbiting environment (e.g., air particle density), the particular application of the satellite (e.g., optical imaging, thermal imaging, radar imaging, other types of remote earth sensor data collection, telecommunications transceiver, scientific research etc.), for instance. In some examples, the system can include one or more passive and/or active systems to manage thermal changes, due to operation of the components themselves, in response to environmental conditions, etc. The computing platform 152 can be configured to adjust the duty cycle of one or more components, transfer power storage and/or use from a given set of batteries to another, or another suitable measure designed to limit overheating within the NEO vehicle 100.

A propellant storage tank 160 is coupled with the engine 106 to generate thrust to counter the forces on the NEO vehicle 100 from drag, or to position the vehicle in the proper orbit. The present and desired orbit can be compared and any adjustments can be implemented by the computing platform 152. For example, based on sensor data, the computing platform 152 can determine spatial information indicative of a current altitude of the satellite, an orientation of the satellite relative to a terrestrial surface, and a position of the satellite relative to other satellites. This data can be compared against a desired altitude, orientation or position. If the computing platform 152 determines an adjustment is needed, the electric propulsion engine 106 is controlled to generate thrust sufficient to achieve the desired altitude, orientation or position.

Figure 10:
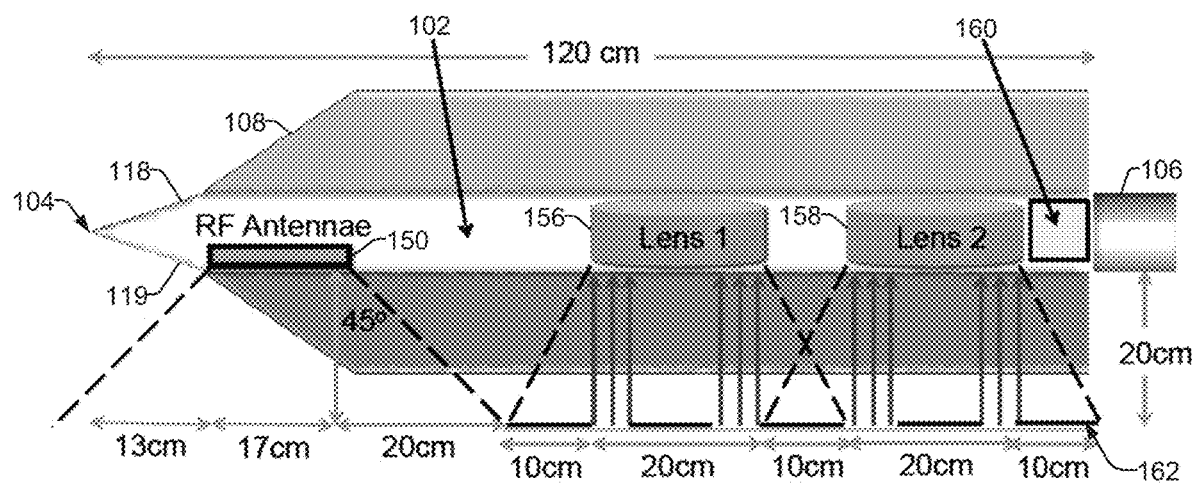
FIG. 10 shows another cross-section of an example satellite illustrating various components in accordance with aspects of this disclosure.

FIG. 10 shows another cross-section of an example satellite illustrating various components and representative dimensions for the NEO vehicle 100, in accordance with aspects of this disclosure. For instance, the vehicle, from leading edge 104 to the far end of the vehicle bus 102, is shown in the example of FIG. 10 as being approximately 120 cm long. Further, from the bottom edge of the engine 106 to the baffle 162 is approximately 20 cm. As shown, the baffle 162 provides a filter for optical imaging systems 156, 158. Moreover, a wide-angle reception band of 45 degrees is illustrated for RF antenna 150. Additionally, FIG. 10 shows a profile of the leading edge 104 and a top bevel 118 and a lower bevel 119.

Figure 11:
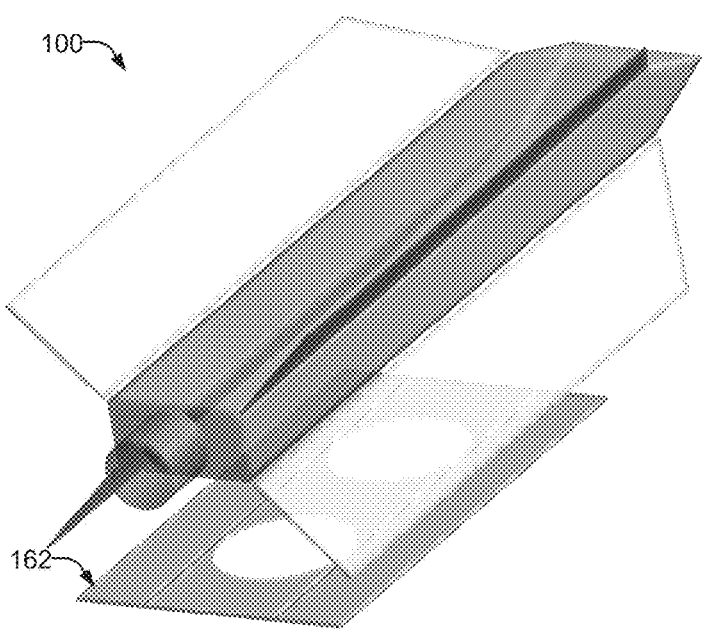
FIG. 11 shows another perspective view of an example satellite in accordance with aspects of this disclosure.

FIG. 11 shows another perspective view of an example satellite. As shown, the baffle 162 is placed between the vehicle 100 and the surface to be imaged (e.g., toward Earth). In this example, two openings are provided to accommodate two imaging systems. However, a single imaging system, or three or more imaging systems, are considered for the disclosed vehicle. Although a one to one correspondence in imaging system to baffle opening is shown, a single baffle opening may be used for multiple imaging systems, or no baffle may be used, depending on the particular application. Although not shown in FIG. 11, the baffle may be attached to the satellite bus in a number of mechanical ways, and the deployment of the baffle may be performed in a number of mechanical ways, for example with a system of springs and latches. Additionally, the center of mass of the satellite should generally be located forward of the center of pressure (e.g., the location where the net aerodynamic force, due to particles impacting the satellite surfaces, acts). Locating the center of mass forward of the center of pressure facilitates passive stability and aids in avoidance of any tumbling motion. Similar considerations are engineered into design of passenger aircraft. The precise location of the center of mass and pressure can be arranged in many ways based on engineering tradeoffs.

In some example imaging systems, a baffle can be used to block a portion of incoming light. Accordingly, only light associated with the imaged surface is transmitted to a lens of an imaging system. The baffle system cooperates with the thin lens and imaging system to provide transmitted light from the imaged surface to a detector (e.g., an array, photodetector, etc.) to collect data and/or images associated with the imaged surface. In accordance with the NEO vehicle described herein, the lens and imaging system are of a thickness sufficient to be fully housed within the vehicle bus (i.e. thinner than the bus height).

Moreover, the satellite systems described herein can employ various forms of electric propulsion devices (e.g., ion engines) such as pulsed plasma thruster (PPT), Hall-effect thruster (HET), microwave discharge, and RF discharge devices. For example, Xe or Ar, both noble gases with relatively high atomic masses, can be used as a propellant. Noble gases are selected because they tend not to damage engine components, and massive atoms efficiently convert energy into momentum. An example electric propulsion engine is manufactured by PhaseFour, Inc. Additionally or alternatively, the engine 106 can comprise an engine with chemical thruster capabilities, such as a micro-thruster type engine.

Figure 12:
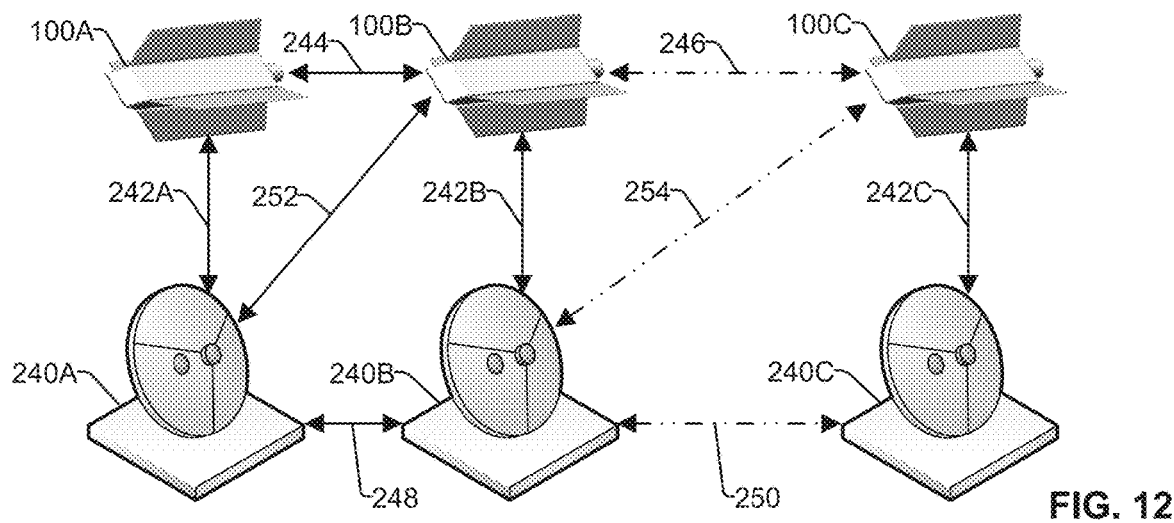
FIG. 12 shows an example of satellites interacting with plural ground stations in accordance with aspects of this disclosure.

FIG. 12 shows an example of satellites interacting with plural ground stations in accordance with aspects of this disclosure. As shown, a plurality of satellites 100A-100C are in a near earth orbit, as described herein. A vehicle-to-vehicle laser communication system may be included to improve data download rates, flexibility and reliability. Each satellite 100A-100C is equipped with communications systems to communicate with other satellites (e.g., laser communications, radio communications, etc.).

For example, satellite 1008 can send and receive information to satellite 100A via link 244 and with satellite 100C via link 246. In a high volume constellation with close spacing at low altitudes, line of sight laser communications to neighbor vehicles will be effective. In the example of 90 satellites in an orbital plane at 1-minute intervals, distance between satellites will be approximately 450 km. Since the horizon from 180 km altitude is more than 1,000 km away, a laser communications system is capable of providing a direct link to multiple satellites in the same orbital plane with minimal atmospheric diffusion effects at low power. Since the vehicles will be oriented along the orbital plane in order to minimize drag and their relative positions change very slowly, the pointing system for the inter-vehicle laser communications may be relatively simple. Using such an inter-vehicle link would enable very high-speed data rate transfer between vehicles, enabling downloads to be handled by a vehicle other than the one collecting an image. Adding this flexibility to the system has several benefits, including filling dead-zone gaps, backup capability if receivers are unavailable, and backup capability if a downlink transmitter on a NEO vehicle becomes disabled.

Figure 13:
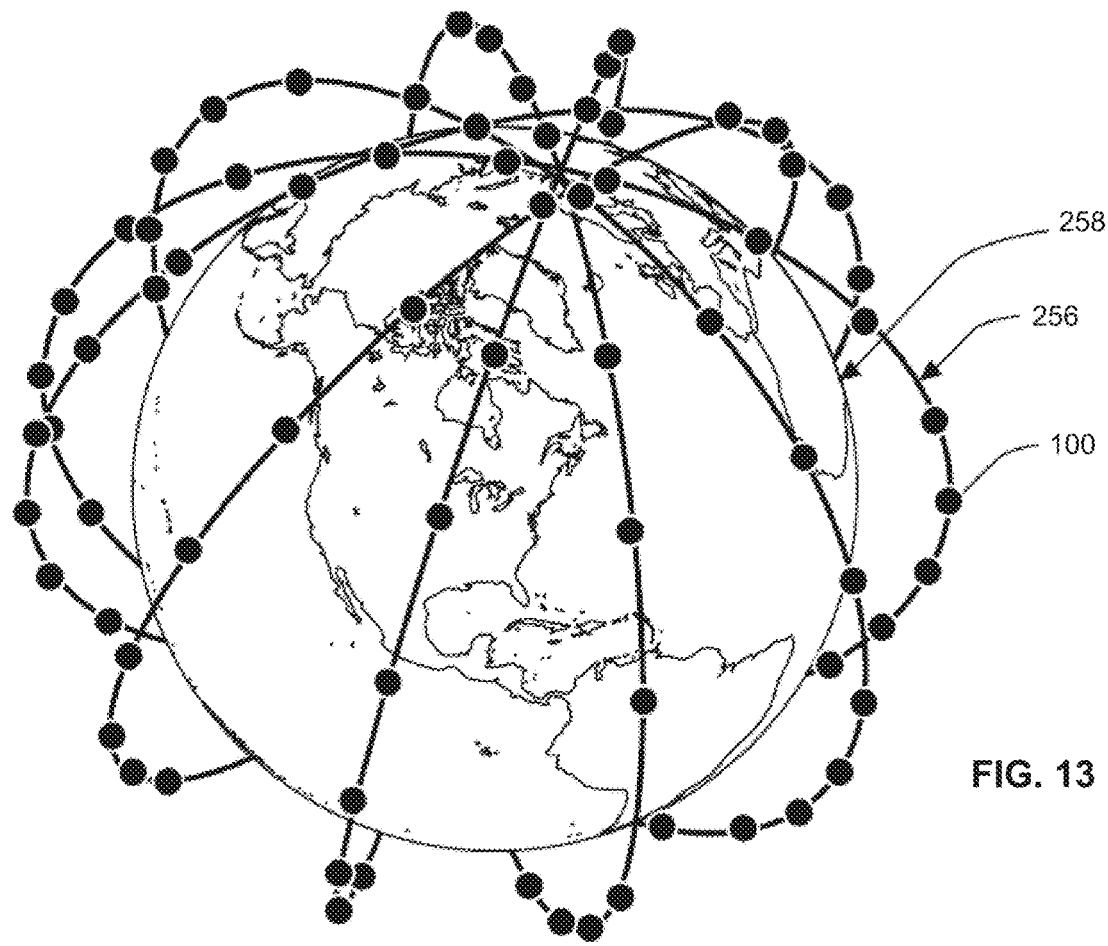
FIG. 13 shows an example of satellite necklaces in accordance with aspects of this disclosure.

Although three satellites are shown in succession, any number of satellites into the tens of thousands can be employed in a satellite constellation, and can be aligned in a single direction of travel in a single orbit, or may be traveling at angles with respect to each other, and occupy multiple orbits (see, e.g., FIG. 13).

As shown, each satellite 100A-100C is configured to send and receive information to and from ground based systems 240A-240C. Each ground based system 240A-240C is configured to communicate with another ground based system via communication links 248, 250. For example, communications links 248 and 250 can be laser based, radio frequency transmissions, wired or fiber optic connections, or a combination thereof. The communication links may utilize dynamic beam shapes to maximize data download during each pass of satellites.

The system further includes a distributed earth receiver system relying on a large number of receivers each downloading data during a satellite overpass. For instance, ground based systems 240A-240C are configured to communicate with satellites 100A-100C to send and receive information via communication links 242A-242C. Additionally or alternatively, a ground based system can communicate with more than one satellite, or vice versa. As shown in FIG. 12, ground based system 240A is communicating with satellite 100A via communications link 242A, and is also configured to communicate with satellite 1008 via link 252. In examples, ground based station 240A can anticipate the arrival of satellite 1008 and adjust one or more antennas to facilitate data transfer. The position of satellites within the orbit can be determined based on information stored in a database and available to each ground station and/or satellite. The database can be updated in response to data received through earlier ground based station communications to improve estimates of a given satellite's location, speed and/or other operational parameters. Moreover, communication between the ground based station 240A and satellites 100A and 1008 can occur simultaneously or in succession.

It is a key element of the current invention that phased array antennas may be used for radio communications, with antennas located on each satellite as well as on each ground based system. For example, phased array antennas permit variable antenna beam shapes to facilitate both signal acquisition (e.g., larger bean width with lower data rates) and signal transmission (e.g., narrower beam width with higher data rates), as described in co-pending application entitled "Radio Frequency Data Downlink For A High Revisit Rate, Low Earth Orbit Satellite System".

The example NEO satellite system described herein is capable of providing imaging, communication services, earth measurements, and other satellite services based on one or more NEO orbiting vehicles operating in long term, stable orbit at altitudes between approximately 180-350 km. Further, the satellite system includes an array of such NEO satellites in sufficient density to enable near-real time coverage of the earth. Benefits of the NEO vehicle 100 with a sustainable orbit would accrue to virtually all other satellite applications, such as communications.

Short revisit times can be described as "near-real time." Traditional LEO and MEO satellites have revisit times from hours to days to weeks, depending on the number of satellites in the constellation. Due to extremely high satellite costs plus high launch costs, satellite constellations are typically limited to a few to a few dozen satellites. Some proposed systems include up to about 100 satellites, promising revisit times down to a day or so.

Near real-time revisit rates with a massive constellation offers many advantages and solves many problems inherent in current satellite systems. One example is the "worst case" revisit time as compared to the average revisit time. Most satellites spend about half their orbit in earth's shadow (i.e., night) resulting in poor or useless images. Adding in cloud cover, up to 70% of earth's surface, sand storms and perspective issues (e.g., images taken around noon cast no shadow and are therefore more difficult to interpret) reduce the number of useful images to about one fifth or less of all images taken.

This sampling problem makes it difficult to plan image capture of a certain spot at a certain time. For many implementations, the average time to a useable image may not be as important as the worst case time, which we define as the time between images that meet a certain set of characteristics (e.g., at a specific location, with specific lighting conditions, with specific weather, during a specific window associated with a specific event, etc.) In this example, getting images of a specific area (e.g., a battlefield or a river flood plain) with a long revisit time constellation can make a worst case scenario push from days into weeks. In this example, a system with a 3-day average revisit time could be overhead at night for several sequential passes, and then encounter cloud cover or dust storms when it is finally overhead with correct lighting. Therefore, an average revisit time of 3 days can become a one or two-week worst case scenario, a delay that reduces or even eliminates the value of the images.

Conversely, with an exemplary revisit time of minutes (e.g., less than an hour, to 10 or fewer minutes), the current NEO system will generally have a vehicle overhead any spot on earth during daylight hours, many times every hour. Furthermore, as clouds and dust storms are not stationary, the probability of having a NEO vehicle 100 overhead during a break in the weather is further increased. Since these statistics are not a purely linear extrapolation of the average revisit times (i.e., they are exponential), worst-case revisit times become much more manageable with the described low revisit time NEO system.

Images are only useful once they are conveyed back to systems on Earth. The NEO vehicle 100 includes a widespread array of receiving stations rather than the normally low number of centralized receiving stations found in use with traditional satellite systems. For example, with three receiving stations (e.g., US, Australia and Europe), a traditional LEO satellite will be within transmission range approximately every 30 minutes (90/3), at best. If the imagery data is available with an inherent delay of a week due to the long revisit time described above, a further 30-minute delay is relatively small.

However, for the current NEO satellite system, with average revisit rates of less than an hour and down to minutes, such a delay would be a large percentage of and possibly greater than the goal. Therefore, data can be downloaded from the NEO vehicles to a large network of low-cost earth receiving stations to enable low-latency data downloads, ideally with latency from time of taking to time of receiving on the order of minutes to tens of minutes.

In one exemplary solution, receiving stations may be mounted atop commercial cellular base stations, of which there are about 300,000 in the US alone. Most such base stations are designed to support cellular communications radially outward, not upward. Therefore, an upwardly pointed radiation pattern can use the open area at the top of the base station tower, directing and receiving all energy to/from an orbiting NEO satellite and away from any interference with the cellular signals.

In order to download sufficient data during an overpass of a single NEO satellite and to meet the size, mass and cost targets of the NEO satellite, a simple antenna with a relatively wide beam will enable a relatively large footprint on earth's surface. For example, a beam with full width half max (FWHM) beam angle of 45° from 100 km altitude would have a circular footprint about 200 km in diameter. Assuming the vehicle's orbital velocity is about 7.8 km/s, a useable receive time of about 60 seconds would result. A narrower beam would reduce this time while a wider beam would increase it.

A tradeoff in the beam width is that as the beam width is reduced, the maximum data rate would typically increase. Hence, a tradeoff is made to optimize how much data can be downloaded during a single pass over a given receiver. A further improvement can be made by using a more highly focused beam on the receiving site and having it track the NEO satellite as it passes overhead. This would enable a relatively long dwell time due to the relatively broad NEO satellite transmission beam, along with relatively high data rates due to the relatively tight receiver beam. Also, since mass of the receiver is not as critical as mass on the NEO satellite, placing a more complex (i.e., heavier) receiver and tracking antenna on the receiving side will reduce overall system cost. In an exemplary embodiment, a NEO vehicle may collect images within a zone in which it is downloading those images to one of the plurality of ground based stations. In this embodiment, images will download to a corresponding ground based station in virtual real-time (e.g., with a delay measured in seconds). As the NEO vehicle exits the zone of acceptance for a first ground based station, it will hand off to another ground based as the NEO vehicle travels, in a manner similar to cellular phone handoffs between cellular base stations In order to ensure low-latency downloads, downloads may occur when a vehicle is passing over long stretches of ocean or other "dead zones", of which the oceans are the largest. In addition to ensuring availability of sufficient receiving stations on islands, receivers may also be placed on ships, buoys, or platforms to receive the images, which can then be transmitted to processing centers via traditional high capacity data links.

The described NEO vehicle 100 that maintains a stable orbit between 180-350 km can be part of an array of satellites in an orbital plane, defined as a satellite necklace (e.g., a single orbital plane with multiple NEOs). Ninety NEOs in a single polar necklace will enable one of these satellites to traverse a given line of latitude about once per minute in a northbound direction assuming orbital times of about 90 minutes, and again on the opposite side of the earth in a southbound direction. In an example, twelve such satellite necklaces may be arrayed, each separated by one hour of longitude, may be able to image any spot on earth on average about once per hour.

In the example of FIG. 13, one or more NEO vehicles 100 can maintain an orbit 256 around the Earth 258, in accordance with the present disclosure. In one example, 90 satellites per necklace can be used, however more or fewer satellites per necklace may be appropriate for a given application. For example, 45 satellites per necklace would space the vehicles at 2-minute intervals, while 180 would space vehicles at 30-second intervals. As a person of ordinary skill will understand, the earth will rotate during the interval between arrivals of two sequential NEOs, with that distance determined by the time separation between the satellites. Different spacing distances may impact other subsystem designs such as optical imaging and radio links, but the concept remains that a NEO satellite system can provide relatively high rates of coverage.

Since the time to revisit the same spot on earth is determined by the time for that spot to rotate under the next necklace, doubling the number of satellite necklaces would reduce the revisit time for any spot on earth to 30 minutes or less, depending on the field of view of the onboard imager or radio. Conversely, halving the number of necklaces to 6 would double revisit times. And reducing the number of necklaces to 4 would triple revisit times. These changes would reduce system cost and complexity, which may be a reasonable tradeoff for certain applications.

Other orbital planes can be utilized, and non-uniform distributions of NEO vehicles could have beneficial applications. For example, non-polar orbits would increase the amount of time spent over populated areas and reduce the amount of total time spent over the poles. In the initially described system of 12 satellite necklaces with 90 NEO vehicles per necklace, twelve NEO vehicles would fly over each pole every minute. Arrays of necklaces with inclinations to the equator of less than 90 degrees could provide shorter revisit times for areas of greater interest. A system of 48 near-polar necklaces with six vehicles per necklace would yield a 15-minute global revisit rate, and higher densities are contemplated for the presently described systems.

Additionally, sequences of satellites with shorter distances between them in a given necklace may be better suited for certain applications. For example, ten satellites separated by a few seconds could provide sequential data on phenomena such as floods, fires or ice melting that could be useful in scientific understanding. A variety of NEO satellite distributions are possible for various applications, each of which can employ the NEO vehicle 100 described herein. In some example constellations, additional NEO vehicles in varied or relatively randomized orbits may reduce revisit times from an hour down to under 10 minutes. In one example, ten thousand to twenty thousand NEO vehicles may provide coverage down to 1-3 minutes between images.

The NEO vehicle 100 may incorporate navigation, cooling, attitude control, radio transmission, optical and radar imaging, power supplies, and digital processing. The resulting satellite can operate in long term, stable orbits at altitudes between approximately 180-350 km, with the capability to capture and transmit images of a given place on Earth on a high frequency basis, be it hourly or even more often.

Different altitudes, even variations of a few to more than ten kilometers, may offer different benefits for certain applications. Wider angle coverage from higher altitudes may be an adjunct to higher resolution coverage from lower altitudes. Combination systems in which SAR radar is combined with optical images may be desirable to operate different sensors (e.g. optical and radar) from different altitudes.

In another exemplary application, it may be beneficial to operate NEO satellites operating at about 200 to 300 km to image orbiting space junk and satellites above them. Thousands of pieces of space junk, from expended launchers to small objects, represent a serious threat to LEO orbiting objects. Tracking such space junk from earth is difficult due to their distance and atmospheric disturbance. Being much closer and moving in independent orbits from those objects can improve tracking substantially. Thus, in some examples, data collection systems (e.g., imaging and/or radar) can be oriented away from the Earth's surface. In this example, the satellite can house various collection systems that have fixed and/or variable orientations, based on the desired scan. Accordingly, in order for a satellite in a NEO to collect data on satellites in the LEO, the data collection system can be oriented opposite the Earth's surface.

Another advantage of the present invention is that the contemplated orbits are "self-cleaning." A NEO vehicle 100 deorbits from influence of drag within days or weeks without thrust, as will any debris from a collision. Deorbit times for vehicles still under control can be accelerated by commanding the vehicle into a high drag orientation. Due to the small size relative to conventional spacecraft, the NEO vehicle 100 should entirely "burn-up" during reentry through the atmosphere. As a result, no space junk is left in orbit when the satellite is decommissioned, and there is substantially no risk of collisions with objects and/or surfaces within the Earth's atmosphere.

For synthetic aperture radar (SAR) radar applications, a smaller number of satellites per necklace and a smaller number of necklaces may be sufficient to provide a desired frequency of useful images thanks to the all-weather and night imaging capabilities of SAR radars. SAR radars employ multiple transmission and reception antenna arrayed in a specific pattern. The pattern is typically longer in one dimension (e.g. the direction of motion) than in the transverse direction. Therefore, a relatively rectangular array of elements may trail behind or be attached to a NEO vehicle to provide the oblong radiation beam needed to construct SAR images. By trailing or attaching such an array of antenna elements, drag will be impacted only marginally since it will be in the particle flow shadow of each NEO vehicle 100.

In the example NEO vehicle 100, due to the large savings in power, a NEO constellation employing radar applications may create near-real time radar imagery of the earth's surface. Considering a SAR as an example, typical satellite-based SAR systems in LEO orbits require average transmit powers in the kilowatt range. Such radars therefore require very large solar arrays to power them and then complex cooling systems to remove the waste heat.

For a NEO SAR system with a 27 times reduction in power, the average transmit power consumption is reduced from, for example, 1 kW to about 50 W. The solar panel size, weight and cooling required would also reduce by 81 times, thereby making such SAR systems that much cheaper to launch and operate. If the relative altitude were to be ¼ instead of ⅓ of the traditional altitude, the savings would increase to 128 times and the SAR example above may require less than 10 watts of transmitted power.

The value and opportunity for this ultra-low power NEO SAR is that such radars can image the earth's surface at night, through clouds, and even through some dust storms. Therefore, a given NEO SAR system would be able to create useful images approximately 100% of the time while reducing the statistical impact of night and cloud cover.

To achieve a SAR, an array of transmit/receive elements is provided with precise spacing, typically at half the wavelength of the transmitted energy. Such elements could be provided on a single NEO satellite with the array attached to or trailing behind the NEO satellite in the direction of motion, thereby creating the typically oblong beam pattern required for SAR. The element array could also be created by a formation of NEO satellites that maintain accurate spacing, with such an arrangement also useful for longer wavelength radars. In both cases, the relative power savings is maintained due to the low altitude of the NEO orbits.

It is also possible to assemble arrays of NEO satellites positioned relative to each other in a formation that may create the antenna array and beam pattern needed for SAR. This may be an optimal approach for longer wavelength SAR applications since spacing between elements is typically related to the wavelength of the RF frequency being used.

The benefits and challenges associated with different orbits can be addressed in response to a desired application's requirements. Combinations of SAR images with optical images provide uniquely useful information. For example, radar may be able to image ground contours through dense foliage that can be complemented by optical images of the foliage. Different frequencies for both radar and optical imaging can also add useful information. It is a benefit of the NEO system that near simultaneous imaging on a high revisit rate (e.g., hourly) provides substantial improvements over traditional satellites at higher altitudes.

In addition, a SAR-equipped satellite could be assigned to shadow an optical imager, thereby providing tight correlation between radar and optical images. Such a combination may provide a more comprehensive understanding of activities on earth's surface than either type of satellite alone can offer. For example, a post-earthquake optical image can identify building damage that might be seen by terrestrial observers while radar images could highlight where vertical displacement has occurred in the building, or is occurring as a precursor to an aftershock. Such combinations today rely on long time lags between the two types of imagers, especially due to the scarcity of SAR-capable satellites.

Orbital planes other than polar are possible as well as a hybrid mix of polar and non-polar planes. The specific orbital plane may be modified for different applications. Land mapping satellites may be concentrated in lower latitudes since that is where the majority of earth's land masses are found. The NEO vehicle 100 described herein can be applied to any orbit in the targeted altitude, from polar to equatorial.

Other Earth observation requirements also benefit from lower altitude orbits. For example, the European Space Agency GOCE satellite configured to provide highly accurate gravitational measurements, was placed in a somewhat lower orbit. The planned orbit was approximately 270 km, with operational orbits achieved at 255 km and 235 km. To stay in the planned orbit for the desired 3-year life, the satellite carried an ion thruster to expel its stored Xe atoms, thereby creating sufficient thrust to counteract the atmospheric drag. Launching sufficient Xe into orbit was both expensive and heavy. However, GOCE was much more massive (approximately 900 kg) than the contemplated vehicles of this invention (approximately 5-20 kg in one example), orbited at approximately 255 km for most of its design life, was not designed with the drag reducing features of the invention, and was not designed to work as a constellation providing low revisit rate earth sensing data. A major earth observation opportunity for NEO vehicles such as disclosed herein corresponds to information transfer (e.g., radio transmissions) for use in the Internet of Things (IoT) technology. As electronic systems expand their direct links between unmanned systems (such as pipelines or driverless vehicles) a NEO satellite may be very effective at monitoring such systems, independent of where the systems are located. Receiving radio transmissions and then retransmitting the information to the next available receiver, such as a ground base station, may become an important advantage in such autonomous systems.

Figure 14:
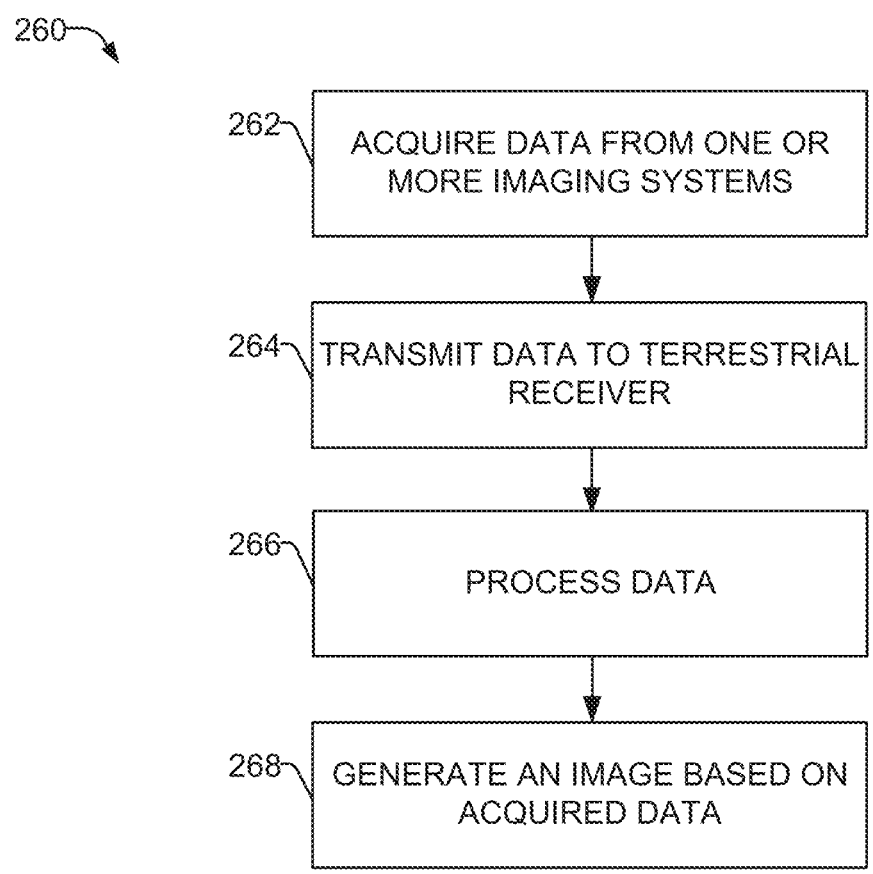
FIG. 14 provides a flow chart of an example method 260 of generating an image from data acquired by an imaging system of one or more NEO vehicles 100, in accordance with aspects of this disclosure.

FIG. 14 provides a flow chart of an example method 260 of generating an image from data acquired by an imaging system of one or more NEO vehicles 100, in accordance with aspects of this disclosure. In step 262, an imaging system (e.g., imaging system 156, 158; radar 150; etc.) from one or more satellites (e.g., NEO vehicles 100) acquires data from one or more sources (e.g. a surface of the Earth; another object orbiting the Earth; etc.). In step 264, the data is transmitted to a receiver, such as at one or more ground stations. The receiver can receive data from a single or multiple imaging systems on a NEO vehicle 100. Additionally or alternatively, the receiver can receive multiple images from multiple NEO vehicles 100, as described with reference to FIG. 12.

In step 266, the image data is processed. For example, the image data can be compiled from multiple sources to enhance image quality, and/or to build an image of a larger area. Moreover, other processing associated with signal transfer, such as buffering, can be performed at this stage. Once data processing is complete, an image is generated in block 268 based on the imaged data from the NEO satellite 100.

In summary, a satellite system has been described that comprises the following features:
Satellite operation in stable orbits at altitudes from 180-350 km;
Vehicle arrays sufficiently dense to enable overflights on approximately an hourly basis;
Solar powered electric propulsion engines on each vehicle providing thrust to counteract drag;
Thin, low drag, resistant, materials and shapes that minimize drag at orbital velocities and these altitudes;
High density array of receiving stations enabling low-latency data downloads;
Laser-based vehicle-to-vehicle communications system;
Platform for optical and radar imagers;
Generate an image from one or more data capture systems;
Provide near real-time revisit rates from satellite to ground based antenna; and
Self-cleaning orbital system for any generated space junk, to name but a few advantages of the present disclosure.

A satellite system is described operating at altitudes between 180 and 350 km relying on NEO vehicles. The system operates at altitudes that are substantially lower than those in which traditional satellites operate, thereby reducing the size, weight and cost of the vehicles and their constituent subsystems, such as optical imagers and radio links. This reduction in size enables a virtuous cycle of further reduction in vehicle drag, which enables lower altitude flight and further reduction in the size of vehicle components, etc., and makes massively large constellations of low cost, low mass vehicles feasible.

The system includes a large number of the low-cost, low-mass, low altitude NEO vehicles, thereby enabling revisit times substantially faster than any previous satellite system. The NEO vehicles spend virtually all of their orbit at the low altitude, high atmospheric density conditions that have heretofore been virtually impossible to consider. Short revisit times at low altitudes enable near-real time imaging at high resolution and low cost. The system further includes a distributed earth receiver system relying on a large number of receivers each downloading data during a satellite overpass. The communication link may utilize optimized beam shapes to maximize data download during each pass. A vehicle-to-vehicle laser communication system may be included to improve data download rates, flexibility and reliability. By operating at such altitudes, orbital mechanics ensure no impact on the space junk issues of traditional LEO orbits and the system is self-cleaning in that any space junk or disabled craft will quickly de-orbit.

What is claimed is:

1. A satellite configured to maintain an orbit between 180 km and 350 km, the satellite comprising:
   a vehicle bus comprising:
      a frontal section having at least one beveled surface configured to reduce drag; and
      a material applied to at least a portion of the at least one beveled surface to provide at least partial specular reflection of incident atmospheric particles, the material selected and the at least one beveled surface configured to reduce drag on and damage to the material from interactions with atmospheric particles incident to the satellite at during orbit by the partial specular reflection of the atmospheric particles.

2. The satellite defined in claim 1, wherein the at least one beveled surface and the material are configured to reduce drag on the frontal section by more than 25 percent compared to the same frontal section geometry with a material that results in fully diffuse reflection.

3. The satellite defined in claim 1, wherein the at least one beveled surface and the material are configured to reduce drag on the frontal section by more than 50 percent compared to the same frontal section geometry with a material that results in fully diffuse reflection.

4. The satellite defined in claim 1, wherein the at least one beveled surface comprises at least one of a) a conical shape, b) a wedge shape, c) a pyramidal shape, or d) a curved shape.

5. The satellite defined in claim 1, wherein the frontal section further comprises a leading edge that includes a first beveled surface of the at least one beveled surface sloping toward a first panel of the vehicle bus and a second beveled surface of the at least one beveled surface sloping toward a second panel of the vehicle bus opposite the first surface.

6. The satellite defined in claim 1, wherein greater than half of the frontal section comprises the at least one beveled surface.

7. The satellite defined in claim 1, wherein a mass of the satellite is less than 20 kilograms.

8. The satellite defined in claim 1, wherein one or more stability fins extend from the bus to provide aerodynamic flight stability.

9. The satellite defined in claim 1 further comprising an engine configured to generate thrust by electric, mechanical or chemical propulsion sufficient to maintain the orbit between 180 km and 350 km.

10. The satellite defined in claim 9, wherein the engine is configured to generate propulsion by use of a Xenon propellant.

11. The satellite defined in claim 9, wherein the engine is a pulsed propulsion system.

12. The satellite defined in claim 1, further comprising a solar energy collection system having a plurality of solar panels to provide power to at least one of the engine, a rechargeable battery, or a component of the satellite system.

13. The satellite defined in claim 12, wherein the solar energy collection system is electrically connected to the plurality of solar panels and configured to store energy collected by the plurality of solar panels.

14. The satellite defined in claim 12, wherein each solar panel is configured to deploy from a folded position during transport or storage to the outwardly extended position during operation.

15. The satellite defined in claim 12, wherein each solar panel is secured to the vehicle at about a 45-degree angle from one of a first or a second panel of the vehicle bus in an outwardly extended position.

16. The satellite defined in claim 12, wherein one or more solar panels of the plurality of solar panels is oriented parallel to the direction of flight.

17. The satellite defined in claim 12, wherein the at least one beveled surface is less than or equal to a 20-degree angle relative to one or more surface panels of the vehicle bus.

18. The satellite defined in claim 17, wherein each of the one or more surface panels of the vehicle bus has a width less than half of a length of the panel, the vehicle bus further comprising lateral side panels between the first and second panels with a height of the lateral side panels less than half the length of the lateral side panels.

19. The satellite defined in claim 18, wherein when the satellite is configured for launch, the plurality of solar panels are folded onto the one or more surface panels of the vehicle bus.

20. The satellite defined in claim 1, further comprising sensors comprising one or more of an optical imager, earth sensor, a radio receiver, or a radar imager.

21. An image or data file generated from data acquired by at least one of the sensors and transmitted from the satellite as defined in claim 20.

22. An image or data file received at the ground station, the image generated at the satellite from data acquired by at least one of the sensors of the satellite and transmitted from the satellite as defined in claim 20.

23. A satellite configured to maintain an orbit having an altitude between 180 km and 350 km, the satellite comprising a vehicle bus comprising:
 a frontal section having at least one beveled surface configured to reduce drag;
 a material applied to at least a portion of the at least one beveled surface to provide at least partial specular reflection of incident atmospheric particles, the material selected and the at least one beveled surface configured to reduce drag on and damage to the material from interactions with atmospheric particles incident to the satellite during orbit by the partial specular reflection of the atmospheric particles;
 an engine configured to generate thrust; and
 a transceiver configured to transmit or receive data from another satellite or at least one ground station.

24. The satellite defined in claim 23, wherein the satellite comprises a controller configured to:
 determine spatial information indicative of at least one of a current altitude of the satellite, an orientation or position of the satellite relative to a terrestrial surface, and a position of the satellite relative to at least one other satellite;
 compare the spatial information of the satellite against a desired altitude, orientation or position; and
 control the engine to generate thrust sufficient to achieve the desired altitude, orientation or position.

25. The satellite defined in claim 23, wherein the satellite comprises an accelerometer, a gyroscope, or a global positioning system.

26. The satellite as defined in claim 23, wherein there are more than six orbital planes.

27. The satellite as defined in claim 23, wherein each satellite is configured to de-orbit within 90 days of loss of thrust.

28. The satellite as defined in claim 23 comprising 48 orbital planes each with six satellites per orbital plane.

29. The satellite as defined in claim 23, wherein the satellite is configured to:
 transmit a first transmission to a first ground station of the at least one ground stations; and
 transmit a second transmission to a second ground station of the at least one ground stations within 15-minutes of the first transmission.

30. The satellite defined in claim 23, wherein the satellite comprises an imaging system configured to collect optical images.

31. The satellite defined in claim 30, wherein the imaging system comprises one or more lenses with a thickness that is at least 80% a height of the vehicle bus, wherein the one or more lenses are oriented generally perpendicular to the direction of flight.

32. The satellite defined in claim 30, wherein the one or more lenses are arranged to produce a folded light path.

33. The satellite defined in claim 30, wherein the imaging system comprises a mechanical device configured to adjust an orientation of the one or more lenses.

34. An image generated from data acquired by the optical imaging system and transmitted from the satellite as defined in claim 30.

35. The satellite as defined in claim 23, wherein the satellite occupies a first orbital plane, the satellite operating in a network of satellites, the network further comprising a second plurality of satellites that occupy the first orbital plane or a second orbital plane different from the first orbital plane.

36. The satellite as defined in claim 35, wherein the first and second orbital planes comprise at least 45 satellites in each plane.

37. The satellite as defined in claim 35, wherein the network comprises more than a thousand satellites.

* * * * *